US012686749B2

(12) United States Patent
Fitzpatrick et al.

(10) Patent No.: US 12,686,749 B2
(45) Date of Patent: Jul. 21, 2026

(54) POLYMER COMPOSITIONS

(71) Applicant: OXFORD MEDICAL PRODUCTS LIMITED, Oxford (GB)

(72) Inventors: Anthony John Fitzpatrick, Oxford (GB); Xue Min, Oxford (GB); Jan Tadeusz Czernuszka, Oxford (GB)

(73) Assignee: OXFORD MEDICAL PRODUCTS LIMITED, Oxford (GB)

( * ) Notice: Subject to any disclaimer, the term of this patent is extended or adjusted under 35 U.S.C. 154(b) by 0 days.

(21) Appl. No.: 18/367,636

(22) Filed: Sep. 13, 2023

(65) Prior Publication Data

US 2023/0416489 A1 Dec. 28, 2023

Related U.S. Application Data

(62) Division of application No. 16/631,903, filed as application No. PCT/GB2018/052051 on Jul. 19, 2018, now Pat. No. 11,795,290.

(30) Foreign Application Priority Data

Jul. 19, 2017 (GB) ...................................... 1711644

(51) Int. Cl.
*C08J 9/36* (2006.01)
*A61F 5/00* (2006.01)
(Continued)

(52) U.S. Cl.
CPC .............. *C08J 9/36* (2013.01); *A61F 5/0003* (2013.01); *A61K 9/0065* (2013.01); *A61K 9/284* (2013.01);
(Continued)

(58) Field of Classification Search
CPC .................................................... A61K 9/0065
See application file for complete search history.

(56) References Cited

U.S. PATENT DOCUMENTS 2,856,268 A 10/1958 Young
7,988,992 B2 8/2011 Omidian et al.
(Continued)

FOREIGN PATENT DOCUMENTS

AU 8554101 1/2002
CN 101588790 A 11/2009
(Continued)

OTHER PUBLICATIONS

Examination report mailed Dec. 20, 2024 in corresponding EP application No. 18749077.6 (6 pages).
(Continued)

*Primary Examiner* — Benjamin J Packard
(74) *Attorney, Agent, or Firm* — Meunier Carlin & Curfman LLC

(57) ABSTRACT

The invention relates to novel a high-volume swelling hydrogel which comprises a plurality of pores which are defined by an interpenetrating network, and/or a semi-interpenetrating network and/or simple cross-linked arrangement of a plurality of one or more species of hydrophilic polymers, optionally together with one or more biocompatible polymers and optionally together with one or more plasticising agents, characterised in that at least some of the pores are at least partially collapsed and/or flattened, and further characterised in that the interpenetrating network and/or semi-interpenetrating network and/or cross-linked arrangement which defines the collapsed and/or flattened pores is substantially unbroken. The invention also relates to a process for preparing such hydrogels, and to their use as an appetite suppressant.

18 Claims, 5 Drawing Sheets

(51) Int. Cl.

| | |
|---|---|
| *A61K 9/00* | (2006.01) |
| *A61K 9/28* | (2006.01) |
| *A61K 9/48* | (2006.01) |
| *C08J 3/075* | (2006.01) |
| *C08J 3/24* | (2006.01) |
| *C08J 9/00* | (2006.01) |

(52) U.S. Cl.
CPC ............ *A61K 9/286* (2013.01); *A61K 9/4816* (2013.01); *C08J 3/075* (2013.01); *C08J 3/246* (2013.01); *C08J 9/0028* (2013.01); *C08J 9/0061* (2013.01); C08G 2210/00 (2013.01); C08G 2230/00 (2013.01); C08J 2205/022 (2013.01); C08J 2207/10 (2013.01); C08J 2305/04 (2013.01); C08J 2305/08 (2013.01); C08J 2339/06 (2013.01); C08J 2371/02 (2013.01); C08J 2405/08 (2013.01); C08J 2439/06 (2013.01)

(56) References Cited

U.S. PATENT DOCUMENTS

| | | | | |
|---|---|---|---|---|
| 2008/0089940 A1* | 4/2008 | Omidian | ............... | C08L 51/02 |
| | | | | 424/487 |
| 2008/0241094 A1* | 10/2008 | Burnett | ............... | A61K 9/2833 |
| | | | | 424/78.01 |
| 2017/0172778 A1 | 6/2017 | Brister et al. | | |
| 2021/0038871 A1 | 2/2021 | Zhao et al. | | |

FOREIGN PATENT DOCUMENTS

| | | | | |
|---|---|---|---|---|
| GB | 806007 A | 12/1958 | | |
| WO | WO-9851408 A1 * | 11/1998 | ............ | C08F 251/00 |
| WO | 2000/09088 | 2/2000 | | |
| WO | 2003/089506 | 10/2003 | | |
| WO | 2008/148047 | 12/2008 | | |
| WO | 2009/012335 | 1/2009 | | |
| WO | 2009022358 A1 | 2/2009 | | |
| WO | 2019152183 A1 | 8/2019 | | |

OTHER PUBLICATIONS

International Search Report and Written Opinion dated Nov. 6, 2018, from International Application No. PCT/GB2018/052051, 19 pages.

Omidian, H. et al. "Elastic, Superporous Hydrogel Hybrids of Polyacrylamide and Sodium Alginate", Marcromolecular Bioscience, 2006, 6, 703-710.

Nwosu, C.J. et al. "Genipin Cross-Linked Chitosan-Polyvinylpyrolidone Hydrogels: Influence of Composition and Postsynthesis Treatment on pH Responsive Behaviour", Advances in Materials Science and Engineering, vol. 2015, 10 pages.

Omidian, H. et al. "Recent developments in superporous hydrogels", Journal of Pharmacy and Pharmacology, 2007, 59: 317-327.

Combined Search and Examination Report under Sections 17 and 18(3) dated Feb. 6, 2018, from related Application No. GB1711644. 3, 6 pages.

Bortolotti, "Twenty-four hour ambulatory antroduodenal manometry in normal subjects (co-operative study)" Neurogastroenterol. Motil. 2000. 12, 231-238.

Examination Report issued in corresponding Indian Application No. 202017004674, dated Jun. 4, 2021 (7 pages).

Office Action and a Search Report received in connection with the corresponding Chinese Invention Patent Application No. CN201880048065X, dated Nov. 18, 2021.

Gemeinhart Richard A. et al., "Effect of compression on fast swelling of poly (acrylamide-co-acrylic acid) superporous hydrogels", Journal of Biomedical Materials Research; vol. 55, Issue1, Apr. 2001, pp. 54-62.

Balamuralidhara et al., "Development of a Novel Biodegradable Superporous Hydrogel for Gastroretentive Application", International Journal of Polymeric Materials and Polymeric Biomaterials, vol. 62, 2013, Issue 10, pp. 524-532.

Hossein Omidian et al., "Elastic, Superporous Hydrogel Hybrids of Polyacrylamide and Sodium Alginate", Macromolecular Bioscience, vol. 6, No. 9, Sep. 2006 (Sep. 15, 2006) , pp. 703-710, XP055054987.

Chen Jun et al., "Synthesis and characterization of superporous hydrogel composites", Journal of Controlled Release, vol. 65, Issues 1-2, Mar. 1, 2000, pp. 73-82.

Chen Jun et al., "Gastric retention properties of superporous hydrogel composites", Journal of Controlled Release vol. 64, Issues 1-3, Feb. 14, 2000, pp. 39-51.

Office Action and a Search Report received in connection with the corresponding Chinese Patent Application No. CN201880048065X, dated Jan. 27, 2022. 15 pages.

Hyojin Park, et al., "Preparation and swelling behavior of chitosan-based superporous hydrogels for gastric retention application", Journal of Biomedical Materials Research Part A vol. 76A, Issue 1 p. 144-150.

Liu, Xinyue, et al. "Ingestible hydrogel device." Nature communications 10.1 (2019): 493:1-10.

Examination Report issued in connection with the corresponding Saudi Arabian Invention Patent Application No. SA520411063, dated Jul. 30, 2022.

Examination Report issued in connection with the corresponding Saudi Arabian Invention Patent Application No. SA520411063, dated Dec. 27, 2022.

Decision of Rejection received in corresponding Chinese Patent Application No. CN201880048065X dated Apr. 25, 2022, 15 pages.

Gemeinhart. Properties of Superporous Hydrogels for Drug Delivery, Thesis, Aug. 1999.

\* cited by examiner

30

28

26

POLYMER COMPOSITIONS

FIELD OF THE INVENTION

The present invention relates to polymer compositions that are suitable for consumption by humans and/or animals in medical and/or non-medical applications. Particularly, the present invention relates to hydrogels which have a high swelling volume and, ideally, a high rate of swelling and/or a robustness when swollen which enables products made therefrom to be to be retained, without degradation and/or digestion, in the stomach of the human or animal. The present invention also relates to a process for the preparation of such hydrogels and their use in medical and non-medical applications, for both humans and animals.

BACKGROUND OF THE INVENTION

Superabsorbent polymers (SAPs) are materials that can absorb and retain extremely large amounts of a liquid relative to their own mass. The total absorbency and swelling capacity properties of SAPs are controlled by the type and degree of cross-linkers used to make them. Low-density cross-linked SAPs generally have a higher absorbent capacity and swell to a larger degree. These types of SAPs also have a softer and stickier gel formation. High cross-link density polymers exhibit lower absorbent capacity and swell, but the gel strength is firmer and can maintain particle shape even under modest pressure. Super absorbent polymers are termed as "hydrogels" when their chemical composition and porous structure allows them to absorb aqueous solutions through hydrogen bonding with water molecules.

As discussed in "Recent developments in superporous hydrogels" by H. Omidian et al in J. Pharm. & Pharmacol. 2007, 59:317-327, superporous hydrogels (SPH) are porous hydrophilic cross-linked structures that are insoluble in water but which have the ability to absorb aqueous fluids up to many times their own weight and also to swell in size. SPHs typically have a three-dimensional network of hydrophilic polymer with numerous pores with an average size larger than 100 µm up to around 1 or 2 mm and it is these pores, which are connected together to form open channel structures, which by capillary action, absorb water very rapidly. Maximum swelling is generally reached in a fraction of a minute and the SPH swells to an equilibrium size.

Hydrogels, particularly "superporous hydrogels" (SPH), were originally developed as a novel drug delivery system which retains/controls the release of drugs in the gastric medium. Their mode of operation typically involves beads of SPH which contain a pharmaceutically active ingredient, and which swell instantly on contact with the stomach fluids and maintain their integrity in the harsh stomach environment whilst releasing the pharmaceutically active ingredient.

As well as drug delivery, hydrogel materials are currently under investigation for a wide range of other medical and non-medical applications, including soaking up water from difficult to access areas; creating watertight seals between objects (for example between flood barrier sections); creating temporary blockages in animal and human Gastrointestinal tract during operations; and providing food additives that assist to reduce appetite and calorie intake in humans and animals (pets). The use of hydrogels as a diet aid or appetite suppressant is believed to provide significant commercial advantages.

Obesity, the medical condition in which excess body fat has accumulated to the extent that it is may have a negative effect on health, is viewed by many as the most serious public health issue of the $21^{st}$ century, with 600 million adults (12%) and 100 million children being diagnosed as being obese in 2015. People are generally considered obese when their body mass index (BMI), a measurement obtained by dividing a person's weight by the square of the person's height, is over 30 kg/m². As well as the obvious negative physical effects on the body of being overweight, obesity causes further complications by increasing the likelihood of various diseases and conditions, particularly cardiovascular diseases, type 2 diabetes, obstructive sleep apnea, certain types of cancer, osteoarthritis and depression.

The cause of obesity in a few cases is due to genetic, medical and mental disorders and also certain medications, however, the vast majority of cases are caused by a combination of excessive food intake, lack of physical activity and genetic susceptibility. Since food intake and exercise are controllable by the overweight individual, it is no surprise that huge efforts are currently being made by governments, the medical profession, pharmaceutical companies and others alike, to introduce interventions which bring about positive social change and the promotion of wise personal choices, which attempt to reverse the trends in obesity for the global population. However, diet, exercise and medication are not effective for everyone and for these people a gastric balloon or surgery to fit a gastric band may be performed to reduce stomach volume or bowel length, leading to feeling full earlier or a reduced ability to absorb nutrients from food.

Gastric balloons, are intra-gastric or stomach-volume occupying devices. Advances have recently been made in the ease of use and patient comfort of these devices, as described in US2017172778, such that a patient swallows a deflated balloon like a pill and its position within the body is monitored using ultrasound, a long thin tube attached to the balloon then allows a physician or other healthcare professional to introduce a gas or other fluid to inflate the balloon within the stomach. For water filled balloons, the tube may be detached and pulled back up the throat and out leaving the balloon in the stomach; after the desired treatment time, the balloon biodegrades and bursts, the water is released and the balloon remnants are excreted. For gas filled balloons, the tube may be retained attached to the balloon and at the end of the desired treatment time, a valve in the tube is used to deflate the balloon and the deflated balloon is pulled back up the throat and out.

In practice, however, even these latest gastric balloons cause problems and some considerable discomfort to the patient both firstly during the swallowing and removal process but also due to the fact that the inflated inserted balloon cannot be compressed by the stomach and this may cause nausea. The buoyancy of the inflated balloon which causes it to float above the gastric media, may also cause blockage or discomfort which will need to be alleviated by antacid treatment. Moreover, although gastric balloon treatment is generally regarded to be "non-surgical" or "procedure-less", it is nevertheless necessary for all gastric balloons to be administered under medical supervision at a clinic. Further, although some balloons are designed to trigger deflation by bursting or biodegradation, it is difficult to predict when this will occur, and it is almost impossible for the patient to terminate the gastric balloon at will.

It is believed by many that the aqueous swelling properties of hydrogels might make them useful as appetite suppressants and numerous workers have investigated a wide range of SPHs which may be used for this purpose. As an example, work by A Sannino which is described in several patent and literature documents including WO2009022358, has led to the development of hydrogel formulations which are being commercialised under the trade names Attiva® and Gelesis 100 ® through a private US company, Gelesis. This product comprises small, micrometre or less-sized, grains of a superabsorbent hydrogel in tablet form and these, once ingested by the recipient before a normal meal, absorb stomach liquids and swell to gels which fill the stomach giving the recipient a sensation of satiety. The superabsorbent hydrogel then shrinks by releasing part of the absorbed water and is excreted from the body. One issue with this product is that it does not appear to be retained in the stomach long enough to make the patient feel satiated for any length of time. Also, there is a need for the patient to take a hydrogel-containing tablet before every normal meal which makes their use somewhat inconvenient for the patient and it may not be effective to counter the effects of eating between meals.

Superporous hydrogels (SPHs) are, as their name suggests, highly porous cross-linked water-swellable super absorbent polymers, but unlike SAPs which need to be dry and have a nano- or micrometre particle size to swell, SPH swell immediately on contact with water regardless of their size or dried state. The pore structure in an SAP typically comprises random closed or semi open cells (pores) whereas SPHs have a structure comprising an interconnected network of cells (pores). In practical terms, the same monomer solution will produce different types of water-absorbing polymer networks, such as non-porous, porous and superporous structures depending upon the presence of foaming agent and a foam stabiliser.

The size of the interconnected pores in SPHs are generally larger than 100 μm to 1 mm and as a result of a water capillary effect induced by these interconnected pores, they are capable of excellent fluid absorption, typically several hundred times their weight in distilled water, and can also swell to an equilibrium size in a short period. The swelling ratio (SR) is a measure of the ability of the polymer hydrogel to absorb water. SR is obtained by balance swelling measurements (using, for example, a Sartorius micro scale with a sensitivity of 10–5) and is calculated using the following formula: $SR=(Ws-Wd)/Wd$. Where Ws represents the weight of the polymer hydrogel after immersion in distilled water for 24 hours, and Wd is the weight of the polymer, prior to immersion of the hydrogel (the polymer hydrogel is pre-dried in order to remove any residual water). Due to the ionic concentrations found in stomach fluids, the in vivo swelling characteristics of SPHs are much lower; typically they absorb 15-20 times their weight in stomach gastric fluids.

However, for many applications, including appetite suppressant applications, it is not only important to ensure that SPHs have a high swelling ratio in terms of the weight of fluid absorbed, it is also necessary for their swelling volume to be as large as possible as this avoids undesirable early exit from the stomach. Swelling volume is believed to be controlled by to the elasticity of the SPH network structure, to the presence of hydrophilic functional groups, the cross-link density, and their porosity. SPHs known so far tend to have a limited volume swelling ability, due to the existence of the pores in the material which are defined by polymer matrices which are not generally elastic, therefore the increase in swelling volume is low.

Migrating motor complexes (or migrating myoelectric complex or migratory motor complex or migratory myoelectric complex or MMC) are waves of electrical activity that sweep through the intestines in a regular cycle during fasting. These motor complexes trigger peristaltic waves, also known as housekeeping waves which facilitate transportation of indigestible substances such as bone, fibre, and foreign bodies from the stomach, through the small intestine, past the ileocecal sphincter, and into the colon. The MMC waves occur every 45-180 minutes during the interdigestive phase (i.e., between meals) and are responsible for the rumbling experienced when hungry. In addition to having a high rate of swelling and a high swelling volume, it is also extremely desirable for superporous hydrogels used in appetite suppressant applications to be sufficiently mechanically robust so that they survive the forces exerted by the muscles in the stomach, for example during phase III interdigestive migrating motor complexes as well as the general peristaltic cycles of stomach muscles.

Cassilly et al. in "Twenty-four hour ambulatory antroduodenal manometry in normal subjects (co-operative study)" Neurogastroenterol. Motil. 2000. 12, 231-238, studied the stomach emptying of a SmartPill and their work shows a strong correlation between the occurrence of interdigestive MMC phase III and the exit of the nondigestive pills. For a SmartPill (>7 mm diameter), the exiting was at 261±22 min (first phase III MMC @ 239±23 min) with an approx. 300 kcal meal. When administered with only water, the gastric residence time was at 92±44 min (first phase III MMC @ 87±30 min). For nondigestive particles smaller than 7 mm, early exiting without phase III MMC is experienced. Thus, any tablet or capsule formulation comprising a superporous hydrogel needs to have a diameter somewhat greater than 7 mm in order to be retained within the stomach for any length of time. Further, it is necessary for this tablet or capsule formulation to swell and achieve such a size within a matter of minutes from swallowing.

The aim of the present invention therefore, is to provide hydrogels and hydrogel-containing compositions made therefrom which are characterised by their ability to exhibit increased swelling volume over known hydrogel materials. Ideally the high-volume swelling hydrogels of the present invention will also be fast swelling and typically will be classed as "superporous". Moreover, the present invention aims to provide high-volume swelling hydrogels or high-volume swelling hydrogel-containing compositions which are highly mechanically robust and which are suitable for use in appetite suppressant applications.

The present invention also aims to provide a suitable process for the preparation of high-volume swelling hydrogels, which process is quick, cost effective and reliable to operate, and additionally, to provide a process for preparing high-volume swelling hydrogel-containing compositions which are mechanically robust.

Yet further aims of the present invention include providing a true "procedure-less" approach to appetite control in overweight/obese animal or human patients which involves ingestion by a patient of an appetite suppressant product comprising one or more high-volume swelling hydrogels according to the present invention, for example in tablet form or some other suitable dosage format. Ideally, said tablet or other dosage format will be available over the counter without the need for a prescription, and without requiring administration by a physician or other healthcare professional to initiate or terminate the process. Advantageously, such an appetite suppressant product will be effective for several days or several weeks at a time, for example up to a week or more, before termination is triggered by automatic degradation or by the consumption of approved chemical or natural food sources, followed by excretion. Further advantageously, the aim of the present invention will also allow patients to be able to ingest more or fewer doses of an appetite suppressant product comprising one or more high-volume swelling hydrogels according to the present invention and also terminate the effects of ingested appetite suppressant product at will. Consequently, the present invention also aims to provide methods for breaking down the appetite suppressant products of the present invention once ingested by the patient, and also to provide appetite suppressant products that are customised according to the required strength and duration of the weight control process.

To achieve the above aims, the present invention provides a high volume swelling hydrogel, which is preferably fast swelling and superporous, comprising a plurality of pores which are defined by a network structure formed by one or more hydrophilic polymers, arranged in the form of one or more selected from an interpenetrating network, a semi-interpenetrating network and a simple cross-linked arrangement, characterised in that at least some of the plurality of pores are at least partially collapsed, and further characterised in that the network structure is substantially unbroken.

The term "collapsed" as used herein is intended to include the pores being "flattened", for example when hydrogel according to the present invention is in the form of a sheet or layer, the pores are "flattened" to lie in the horizontal plain of said sheet or layer of hydrogel.

By "substantially" it is understood that at least 50%, preferably at least 80% and most preferably at least 90%, of the network structure in a representative sample of a high-volume swelling hydrogel according to the present invention, is unbroken.

By "unbroken" it is understood to mean that the network structure is not ruptured and that the integrity of the interconnected pore structure is maintained.

The present invention further provides a composition comprising one or more high-volume swelling hydrogels of the present invention, optionally together with one or more biocompatible polymers and further optionally together with one or more plasticising agents.

Advantageously, the high-volume swelling hydrogels of the present invention have excellent mechanical strength properties. Consequently, preferred high-volume swelling hydrogels according to the present invention comprise one or more hydrophilic polymers which are selected to impart toughness or enhanced mechanical strength characteristics to the high-volume swelling hydrogel. Particularly preferred hydrophilic polymers that are useful to impart toughness are derived from or formed from at least one selected from acrylamide, N-isopropylacrylamide, poly(2-acrylamido-2-methyl-1-propanesulfonic acid, poly(di(carboxylatophenoxy) phosphazene and alginate.

Alternatively, the invention provides compositions that comprise a mixture of one or more high-volume swelling hydrogels and one or more mechanically strong hydrogels. More specifically, the invention provides compositions that comprise at least one first component which comprises one or more high-volume swelling hydrogels which comprise a plurality of pores that are defined by a network structure formed by one or more hydrophilic polymers, arranged in the form of one or more selected from an interpenetrating network, a semi-interpenetrating network and a simple cross-linked arrangement, characterised in that at least some of the plurality of pores are at least partially collapsed and further characterised in that the network structure is substantially unbroken; and at least one second component which comprises one or more mechanically strong hydrogels.

Suitable mechanically strong hydrogels are typically non-super porous and slow-swelling hydrogels, and are superabsorbent polymers (SAP) which are hydrophilic networks that can absorb and retain huge amounts of water or aqueous solutions. Preferably, they can uptake water as high as 100,000%. Further preferably, the one or more mechanically strong slow swelling non-superporous hydrogels are selected from double network hydrogels (DN), nanocomposites hydrogels (NC), topological hydrogels (TP), macromolecular composite hydrogels (MMC). Particularly useful slow swelling non-superporous hydrogels include, but are not limited to, poly (2-acrylamido, 2-methyl, 1-propane-sulfonic acid) (PAMPS)-polyacrylamide (PAAm) double network hydrogel, Argarose-Hydroxyethyl Methacrylate (HEMA) double network hydrogel, Alginate-PAAm double network hydrogel, poly (N-isopropyl acrylamide) and poly (N-isopropyl acrylamide)-laponite nanocomposite hydrogel. Although such slow swelling non-superporous hydrogels have a limited swelling rate, they may nevertheless have a reasonable swelling capacity of up to 15-20 folds in terms of volume increase from xerogel to fully swollen state. When reaching their swollen equilibrium, the non-superporus hydrogels can still retain a maximum engineering compression strength of 2-3 MPa or larger, however, generally with limited volume swelling ratio. Suitable slow swelling non-superporous hydrogels are porous even though their percentage porosity will be lower than the high-volume swelling superporous hydrogels of the present invention The above compositions are ideally suited to provide a product formulation for use in appetite suppressant applications, which product formulation comprises at least one first component which comprises one or more high-volume swelling hydrogels according to the present invention; and, optionally, at least one second component which comprises one or more slow swelling non-superporous hydrogels. When a second component is used in addition to the first component, the resulting product is herein referred to as "a multi-component product". A preferred multi-component product comprises one or more discrete regions or areas comprising an at least one first component, and one or more discrete regions or areas comprising an at least one second component. In this embodiment, the one or more first and one or more second components are preferably moulded together either to create single sample which may be administered directly, or made into a desired product formulation e.g. a capsule, tablet, or lozenge, which (in either alternative) will contain discrete regions or areas of either the first or the second components.

In an alternative multi-component product formulation, separate and discrete regions of the product may be formed by using different types of "beads", a first type of bead preferably comprising the first component which comprises one or more high-volume swelling hydrogels, and a second type of bead preferably comprising the second component which comprises the one or more slow swelling non-superporous hydrogels. The beads may be any regular or irregular shape including sphere, cylinder, ellipsoid, preferably with a minimum dimension (prior to ingestion by a patient) of around 8 mm. The beads are preferably made by moulding or casting the monomer starting materials in a mould followed by polymerisation. Desired ratios of the first and second types of beads are preferably packaged together to produce the product formulation (such as a capsule, tablet or lozenge, preferably a standard 000 capsule or other form of capsule) that can be swallowed. Ideally, the first and second types of beads are either connected together for example via a linkage, such as fibrous materials (including suture material that may be dissolvable, non-dissolvable, natural or synthetic, or any other thread materials) to form a string, or by encapsulating or wrapping them, for example in a membrane or a mesh or a capsule. Ideally following ingestion, the hydrogel "beads" are released into the stomach of the patient as a result of the linking materials and/or wrapping membrane and/or mesh materials being soluble or degraded by the stomach environment, or breakable under the forces exerted during the swelling of the ingested hydrogel "beads", and excreted. Each individual hydrogel "bead" preferably has (1) a full-swollen volume smaller than the diameter of pylori of the patient (human or animals); and (2) a larger full-swollen volume to allow its retention in the stomach.

Each bead preferably has minimum dimension from 1 mm up to 15 mm, preferably 1 mm up to 12 mm, further preferably 1 mm up to 10 mm. An ideal bead is at least substantially spherical or at least substantially cylindrical with a minimum diameter of at least 3 mm. The preferred orally administrable formulation will contain a total number of first and second types of beads is preferably up to 10, further preferably 2 to 5, and optimally 3, however the precise number will depend on the shape and volume of the orally administrable formulation. In some cases, one bead will be used and this will preferably be a high-volume swelling hydrogel of the present invention. The preferred orally administrable formulation will contain a ratio of first to second type of bead in the range 4:1 to 1:4, further preferably in the range 1:2 to 2:1, and ideally in the ratio 1:1.

The size of the product formulation (such as a capsule, tablet or lozenge, preferably a standard 000 capsule or other form of capsule) and the number of beads contained therein will be constrained by the size of the capsule casing; wrapping the one or more hydrogel beads in a membrane or mesh will enable a higher number of beads to be used. However, ultimately, the number of beads will be governed by the size of product formulation that is acceptable to a patient for oral administration, typically this will be around 20 mm×40 mm, preferably around 14 mm×20-25 mm.

In a further alternative embodiment, the present invention provides a single-component product formulation, that is a capsule, tablet or lozenge, preferably a standard 000 capsule or other form of capsule, that can be swallowed, which comprises one or more beads that comprise a first component (comprising one or more high-volume swelling hydrogels), in the absence of any beads that comprise a second component (comprising one or more slow swelling non-superporous hydrogels). The size of these one or more first component-containing beads, the size and type of the resulting product formulation, the means by which two or more beads are connected and/or packaged together and the total number of beads used in a single-component orally administrable product formulation, are as described above. Also as described above, each individual hydrogel bead preferably has (1) a full-swollen volume smaller than the diameter of pylori of the patient (human or animals); and (2) a larger full-swollen volume to allow its retention in the stomach. As above, the beads may be any regular or irregular shape including sphere, cylinder, and ellipsoid, preferably with a minimum dimension (prior to ingestion by a patient) of around 8 mm.

In another further alternative arrangement, the invention provides a multi-component product formulation comprising a mixture of separate discrete regions or areas in a "core-shell" format. In this arrangement, one of the first and second components is used to form one or more "core(s)" that is or are encapsulated or surrounded by one or more "shell(s)" made from the other of the first and second components. Preferably, the first component (which comprises one or more high-volume swelling hydrogels of the present invention) is used to form the "shell" and the second component (which comprises one or more slow swelling and non-super porous hydrogels) is used to form the "core".

In a preferred multi-component product formulation, the first and second components may originate from a single basic hydrogel base material; this is particularly convenient when the hydrogel base is also a mechanically strong hydrogel. In this embodiment, the first component will contain said hydrogel base after it has been made superporous and treated to compress at least some of its pores to produce a high-volume swelling hydrogel and the second component will contain pristine hydrogel base.

The multi-component hydrogel product formulation may also comprise at least one further component in addition to or as an alternative to the second component. Preferably, the at least one further component will comprise one or more superporous hydrogels, for example, of the type already known in the prior art. In some cases the same hydrogel base may be used to prepare the one or more further component as used to make either the first component or the second component (if the latter is present). The at least one further component is preferably said hydrogel base after it has been made super-porous.

Whilst the product formulations of the present invention are designed not to block the oesophagus or lower GI tract, it is possible that an unforeseen accident may happen. Also, it is desirable that the appetite suppressant formulation is able to be terminated easily without the need for surgical, endoscopic or other unpleasant medical interventions. The present invention combats these issues by the use of a trigger or emergency exiting mechanism to breakdown of the product formulation into a form which is easily excreted by the patient. The 'breakdown trigger' can have variety of forms so long as it is effective and efficient in the breakdown process and is safe to be used by the patient, Preferred breakdown triggers include, electromagnetic waves (e.g. light, heat), mechanical waves (e.g. ultrasound) or chemicals.

Depending the nature of the hydrogel, the breakdown trigger could be, but is not limited to, one of the following:
(1) a solution with certain chemical or chemicals which attack the crosslinking groups;
(2) an alkaline solution which reduces the mechanical strength of a pH-sensitive hydrogel;
(3) a high intensity focused ultrasound (HIFU) device that targets hydrogel-containing compositions;
(4) a heat, light, electrical signal delivered to the blockage point by endoscopic or another capsule like device that will trigger the response of temperature-, light-, electricity-sensitive hydrogels.

As an Example, hydrogels of the present invention can be designed to have reversible crosslinking that can be attacked by certain chemicals. Whilst the reversible crosslinks will be stable in the stomach environment, the chemical trigger is preferably either something that is not normally consumed in daily life or something that exists in food but in an amount which is too low to cause an immediate breakdown of the hydrogel. The quantity and concentration should be strictly controlled within the allowance that can be found in the regulations given by the established authorities. The potential reversible crosslinking and their antidotes might include one or more of the following Table 1:

TABLE 1

| Hydrogel base | Crosslinking agent | Reversible bonding | Potential Breakdown Triggers |
|---|---|---|---|
| Acrylamide | N,N'-bis(acryloyl) cystamine (BAC) | Disulfate bonds | Glutathione/ Cysteine-HCl/ Lycopene/ Procyanidine |
| N-isopropylacryl-amide | N,N'-bis(acryloyl) cystine (BISS) | Disulfate bonds | Glutathione/ Cysteine-HCl/ Lycopene/ Procyanidine |
| Alginate | Calcium chloride, Calcium sulphate | Calcium centred ironical bonding | Ethylenediamine-tetraacetic acid & its salts Porphine/heme/ Chlorophyll etc. |
| poly-(di(carboxylato-phenoxy) phosphazene) | Calcium chloride, Calcium sulphate | Calcium centred ironical bonding | Ethylenediamine-tetraacetic acid & its salts Porphine/heme/ Chlorophyll etc. |

When in use as an appetite suppressant, the above described product formulations are swallowed, where used, the encapsulating mesh, membrane or capsule casing may dissolve in the stomach juice, or may be designed to rupture under the forces exerted by the swelling hydrogel, and the high-volume swelling hydrogel of the present invention will swell quickly (within 10 to 30 minutes) to a size larger than the pylorus, preferably a diameter>25 mm, further preferably >30 mm. As discussed above, housekeeping waves are expected at around 90 min under fasting conditions and at around 220 min when in a fed state with a 300 kcal low calorie meal. In a preferred embodiment, high-volume swelling hydrogels will be able to survive these housekeeping waves in the first a few MMC cycles, before the stronger slow swelling non-super porous hydrogel reaches a sufficiently large size within a few hours.

In case of an unexpected blockage, the patient will be advised to take a proton pump inhibitor (PPI) to raise the stomach pH so that it can be a more suitable environment for the preferred antidotes (e.g. when EDTA is used as an antidote, it will be more efficient under an alkaline environment because this chemical dissolves in alkali). If the stomach remains at pH 1-3 while we give the patient the antidote (with a pH of 8-10), the stomach juice may neutralize the antidote and as a result, it may slow down the degradation of the gels. A 100-500 ml solution consisting of ethylenediaminetetraacetic acid (5-50 mM) and glutathione (5-50 mM) dissolved in 0.1-0.7M NaOH (final pH 8-10) is administrated to the patient. The solution will ideally degrade both the high-volume swelling hydrogel(s) and also the slow swelling non-super porous hydrogel(s) to a size that can pass the gastro-intestinal tract in around 10-30 min.

The present invention also provides a process for preparing a high volume swelling hydrogel which is preferably fast swelling and superporous, the process comprising the steps:

a) providing an initial hydrogel, which comprises a plurality of pores which are defined by a network structure formed by one or hydrophilic polymers arranged in the form of one or more selected from an interpenetrating network, or a semi-interpenetrating network or a simple cross-linked structure, and which is made from a composition comprising one or more hydrophilic polymers; and b) treating the initial hydrogel with a compressive force suitable to collapse and/or flatten at least some of the pores of the initial hydrogel whilst maintaining the integrity of the network structure, (that is, without substantially breaking the interpenetrating network, or a semi-interpenetrating network or a simple cross-linked structure), thereby to yield the high-volume swelling hydrogel.

Preferably the initial hydrogel is a fast swelling super-porous hydrogel, and the resulting post compression product is a high-volume fast swelling superporous hydrogel.

In a preferred process one or more additives may be added to the initial hydrogel. Suitable additives may include bio-compatible polymers and plasticising agents;

In a further preferred process, either in addition to or as an alternative to the use of one or more additives, the initial hydrogel may be treated under suitable conditions to improve its plasticity prior to performing step b);

Preferably, the initial hydrogel will comprise one or more hydrophilic polymers chosen (as discussed above) to impart improved mechanical properties or toughness to the high-volume swelling hydrogel made in step b) of the process.

Preferably, the initial hydrogel has an initial thickness which is reduced following the application of the compressive force in step b) such that the resulting high-volume swelling hydrogel has a thickness after compression (post compression thickness) of 50% or less, preferably 30% or less and highly preferably 15% or less of the initial thickness, (i.e. the thickness of the initial hydrogel is reduced by at least 50%, preferably by at least 70% and highly preferably by at least 85%, respectively, following compression). Preferably the median compression ratio in one dimension is 2-16 times, which 8 times being particularly preferred. The compression ratio characterises the extent of compression in terms of the geometry change rather than the applied forces. For instance, when the compression ratio is noted as being "8 times", this means that a sample which starts as having a dimension of 16 mm will have a corresponding post-compression dimension of 2 mm. The "compression pressure" is not used to characterise the compression as this is a function of sample strength, compression temperature, and the humidity of the environment. In some applications, it is preferred to produce a sheet of the high-volume swelling hydrogel, which sheet will ideally be compressed to have a thickness of 3 mm or less, preferably 2 mm or less and particularly preferably 1 mm or less.

Advantageously, the high-volume swelling hydrogel of the present invention as made by the process of the present invention, exhibits a swelling volume which is at least two times greater than and preferably at least 5 times greater than the swelling volume exhibited by the initial hydrogel.

The initial hydrogel can be made from a plurality of any suitable species of one or more hydrophilic polymers. The hydrophilic polymers may be derived from naturally occurring polymers and monomers, from synthetic polymers and monomers, or from mixtures of naturally occurring and synthetic polymers and monomers. Preferably, the hydrophilic polymers are hydroxylated polymers, and further preferably, the hydrophilic polymers are selected from $C_1$-$C_6$-alkylcelluloses, hydroxy-$C_1$-$C_6$-alkylcelluloses, hydroxy-$C_1$-$C_6$-alkyl-$C_1$-$C_6$-alkyl-celluloses. Further preferably, the hydrophilic polymers are selected from methyl-cellulose, ethylcellulose, n-propylcellulose, hydroxyethyl-cellulose, hydroxy-n-propylcellulose, hydroxy-n-butylcellulose, hydroxypropylmethylcellulose, ethylhydroxyethylcellulose, carboxymethylcellulose, carboxymethylstarch, chitosan, alginate, gelatin, cationic dextran, (e,g, dextran sulfate, dextran phosphate, dimethyl aminodextran, diethyl aminodextran, cationic dextrin, polyetherimide, heparin, hyaluronic acid, chondroitin, chondroitin sulfate, heparan sulfate, polygalacturonic acid, polyanuronic acid, polygalacturonic acid polyarabinic acid and polylysine. In some cases, one or more hydrophilic polymers may be made by the polymerisation and copolymerisation of monomers selected from $C_1$-$C_6$-alkenyl amides (e.g. to make polyacrylamide) and $C_1$-$C_6$-alkenyl acids (e.g. to make acrylic acid). Other possible polymers include poly(acrylamide), poly(2-acrylamido-2-methyl-1-propanesulfonic acid) and poly(N-isoacrylamide).

Chitosan is a preferred hydrophilic polymer. Chitosan is a linear polysachaccaride composed of randomly distributed $\beta$-(1-4)-linked D-glucosamine (deacetylated unit) and N-acetyl-D-glucosamine (acetylate unit). It is made by partially removing the acetyl groups from the parent molecule chitin, by treating shells of crustaceans with an alkali such as sodium hydroxide.

Chitosan cross linked with poly (N-vinyl-2-pryrolidone (PVP) provides a suitable initial superporous hydrogel with a semi-penetrating network comprising a primary cross-linked chitosan network loosely penetrated with PVP, i.e. PVP is not chemically bonded to the chitosan. It is useful to dissolve the chitosan in a weak acid medium (e.g. acetic acid) prior to crosslinking. For other polymer systems, other acids may be more favourable, for example a poly(acrylic acid-co acryliamide) system may prefer acrylic acid.

One or more biocompatible polymers may optionally be used in conjunction with the hydrophilic polymers and suitable examples are selected from one or more of polyallyl alcohol, polyvinyl alcohol, polyacrylic acid, polyethylene glycol and poly(N-vinyl-2-pyrrolidone) (PVP), and these may be copolymerised with one or more further polymers, for example, acrolein.

Other suitable initial hydrogels (preferably initial superporous hydrogels) may be prepared by forming a mixture comprising a plurality of one or more hydrophilic polymers, and optionally one or more biocompatible polymers, and subjecting the mixture to the addition of one or more cross-linking agents, and/or to irradiation (for example with a high-energy ionizing radiation such as electron beam (e-beam), gamma or x-ray radiation) and/or other conditions suitable for generating the interpenetrating network, or the semi-interpenetrating network or the simple cross-linked structure of the hydrogel (such as sulfur vulcanisation or other suitable chemicals, optionally in conjunction with heating and/or increased pressure). It is important to control the degree of cross-linking, however, so that it does not interfere with the swelling volume ratio of the product.

As their name suggests, superporous hydrogels are naturally porous, and as described above, their pores are defined by their network/cross-linked structure. The size of the pores depends on the composition of the hydrophilic polymer, and optional biocompatible polymer and the effect one ingredient has on the others, for example PVP has an effect on the aqueous solubility of chitosan which effects pore size. However, it is particularly preferred that an initial superporous hydrogel comprises pores which have an average size in their largest dimension of between 100 μm and 500 μm, ideally between 200 μm and 500 μm. This may be the natural pore size for some superporous hydrogels which may be used as the initial superporous hydrogel, or in other cases pores with this size characteristic will need to be generated, for example by the addition of a porogen and/or a foaming agent and/or an acid and a carbonate (for example $NaHCO_3$) to the composition from which the initial superporous hydrogel is made, or alternatively, by subjecting the initial superporous hydrogel once made, to a freeze drying process. The freeze drying step may be carried out by first freezing the superporous hydrogel in a conventional freezer or using an ultra-low temperature freezer (−20° C. to −86° C.), and then using freeze drying apparatus (−50° C. to −80° C.), to give material with the desirable pore size (between 0.1 μm and 5 mm).

In general, the more dilute the mixture of polymers, the larger the pore size. Also, the amount of foaming agent and/or stabilizer will affect pore size. Finally, the lower the temperature of freezing, the smaller the pore size.

The high-volume swelling hydrogels made by the process of the present invention will preferably contain the same number of pores per unit weight as the initial hydrogel from which they are made. A suitable initial hydrogel will contain a pore volume of 70-90% and this will preferably result in a high-volume swelling hydrogel with a post-compression pore volume of 10-30%.

A further important characteristic of the initial hydrogel which has an impact on how effective the compressive force will be in step b) of the process of the present invention, is the plasticity of the initial hydrogel. This may be an inherent property resulting from the choice of hydrophilic polymers and the optional biocompatible polymers, but for many hydrogels which have a fairly rigid structure, the plasticity needs to be improved. The addition of a plasticising agent (for example water or an ester such as a sebacate, an adipate, a terephthalate, a dibenzoate, a gluterate, a phthalate, a azelate, and blends thereof), although may be used it is undesirable when the hydrogel is to be used as a gastric appetite suppressant where using a minimal number of chemicals will reduce the risk of unwanted side effects, thus, in a preferred process of the present invention, the initial hydrogel is treated under conditions which will reduce its glass transition temperature and thereby increase in its plasticity. The present Applicant has found that compressing the initial hydrogel under heat treatment or a damp environment or both (for example treating it with steam), is an excellent way to make the initial hydrogel more malleable—i.e. rollable without cracking.

As described above, the key feature of the high-volume swelling hydrogels of the present invention is that at least some of the pores are at least partially collapsed and/or flattened, i.e. the space between the polymer chains (in other words the space as defined by the network/cross-linked structure in the initial superporous hydrogel), is at least partially reduced, and preferably eliminated. The other key feature is that the interpenetrating network and/or semi-interpenetrating network and/or cross-linked arrangement which defines the collapsed and/or flattened pores, is substantially unbroken, i.e. the structure, although now collapsed/flattened, is substantially not damaged or compromised. It is the high plasticity characteristics of the initial hydrogel which particularly influences the ability of the resulting high-volume swelling hydrogel to achieve the second of these features.

Step b), that is, the collapsing/flattening of the pores in the initial hydrogel, is conveniently effected by applying a compressive force using any suitable means or apparatus. It is particularly convenient to pass the initial hydrogel material being compressed between one or more pairs of rollers and/or use one or more plates to exert pressure onto the hydrogel and/or use a vacuum to assist in providing the compressive force. The one or more rollers or plates may be made of any suitable material including glass, plastic, ceramic or metal, and the compressive force may be applied mechanically by hand. In this way, the initial hydrogel has an initial thickness which is squashed/flattened so that it becomes thinner, i.e. the initial thickness is reduced 2-16 times, and the reduced thickness is referred to here as the "compressed thickness". Following the application of a compressive force, the size of the pores of the high-volume swelling hydrogel will preferably be reduced by at least a factor of 2 in all dimensions.

It is of benefit to apply the compressive force in step b) of the process of the present invention at elevated temperature because a material will be deformed by an external force at a temperature above its glass transition temperature (Tg). Conveniently, in the case of material which has been plasticised, as described above, it is only necessary to use a temperature of around 30 to 60° C. Ideally, further processing of the compressed material will be carried out at a temperature above 30° C., or quickly at normal room temperature before the temperature of the material falls below 30° C. post steaming Following application of a compressive force, the elevated temperature may be reduced, for example to ambient temperature, to "set" the compressed thickness of the high-volume hydrogel.

Preferably, the high-volume swelling hydrogels of the present invention are formed by compressing the initial hydrogel, to a thickness of between 0.5 mm and 2 mm, and as described and demonstrated in the specific examples given below, such a high-volume swelling superporous hydrogel is able to swell to 6 times the maximum volume swelling ratio of the initial hydrogel.

Generally speaking, the ionic nature of the high-volume swelling hydrogel will influence the observed speed of swelling degree of swelling, for example in the case of a cationic SPH which will contain a primary, secondary or tertiary amine functional group (such as chitosan) which can be protonated in acidic media (such as gastric media), these positive charges repel each other and result in stretching/expanding at low pH. This effect is reduced when cationic superporous hydrogels are placed in alkaline media, but here anionic superporous hydrogels swell best in alkaline media by the analogous repulsion of negative charges. Non-ionic electrolytes which are neither anionic nor cationic, do not generate ions which repel one another but they do nevertheless swell, albeit by a reduced amount compared with cationic or anionic superporous hydrogels, by being "pumped up" by the aqueous media in which they are immersed.

A particular advantage of the high-volume swelling hydrogels of the present invention is the ability to use them in orally-acceptable formulation for applications which require a fast speed of swelling and a particularly high swelling volume. The Applicant has found that their high-volume swelling hydrogels are easily formulated into any orally-acceptable formulation, and their thinness post application of a compressive force enables a higher weight of the high-volume swelling hydrogel to be used in a given formulation. For example, more high-volume fast swelling hydrogel can be packed inside a tablet/capsule casing that has so far been possible with the prior art superporous hydrogel granular materials. This has the positive effect that not only is the swelling volume of the high-volume swelling hydrogel inherently greater than the prior art superporous hydrogel granules used previously, but there is more high-volume swelling hydrogel in the formulation available to swell.

The process of the present invention produces dry desiccated high-volume swelling hydrogels, however, to make this material more malleable and able to be more readily swallowed, it is preferable that it is at least partially swelled with water. Consequently, the preferred high-volume swelling hydrogel is in the form of a soft gel, and typically this is as a result of i) the steps taken to improve the plasticity of the initial hydrogel prior to the compression step in the process of the present invention and/or ii) by the addition of 10% by volume of water post compression. By contrast, the prior art superabsorbent materials are typically dry and granular. A soft gel consistency has the advantage over the prior art granular superabsorbent hydrogel (e.g. by Gelesis) in that it has a comparatively strong network/cross-linked structure before it is immersed in water (or gastric fluids). This means that the high-volume swelling hydrogels of the present invention, particularly those produced by the process of the present invention, are able to retain their absorbed water (or gastric fluids) for many days, if not weeks. By contrast, the prior art dry superabsorbent polymer granules only form their gel structure when they react together in an aqueous medium and, as mentioned above, this absorbed water is lost from the gel after only a few hours.

The Applicant has further found that the volume swelling ratio of the resulting high-volume swelling hydrogels of the present invention can be optimised when they are made superporous using a freeze drying process and particularly preferably by the addition of at least 80% (preferably at least 90%) by weight of water to the initial hydrogel prior to forming the pores using a freeze drying process.

Advantageously the high-volume swelling hydrogels of the present invention may be compressed into a flat sheet which may be rolled, and/or folded and/or pleated and/or corrugated and/or spooled and/or concertinaed prior using them as part of an orally acceptable formulation. Alternatively, the SPH of the present invention may be moulded or cut into any desired shape, such as a sphere, donut shape, bunting, collapsed hollow sphere etc. before using as part of an orally acceptable formulation. An oral capsule is a particularly preferred formulation.

The high-volume swelling hydrogel prepared of the present invention and as prepared by the process of the present invention, may be used in the treatment and/or prevention of one or more medical conditions which can include, but are not limited to, obesity and diabetes.

Highly preferably, the high-volume swelling hydrogel prepared of the present invention and as prepared by the by the process of the present invention, may be used as an appetite suppressant.

In a further aspect, the present invention provides dosage regimen for administering to a patient suffering from one or more medical conditions, for example selected from obesity and diabetes, comprising orally administering to the patient a first dose of an orally acceptable formulation comprising the high-volume swelling hydrogel of the present invention in an amount of or a number of samples which will swell upon ingestion to fill up to 80%, preferably up to 60%, further preferably up to 50% of the volume of the stomach of the patient.

In a preferred dosage regimen for treating an obese or diabetic patient, an initial large first dose of preferably greater than 3, preferably at least 5 and further preferably at least 20 orally acceptable tablets or capsules (any other suitable product formulation may also be used, preferably 000 size capsules) comprising one or more high-volume swelling hydrogels of the present invention are administered to the patient. This is then optionally followed by a second, and optionally further subsequent, doses preferably containing up to 5 orally acceptable tablets or capsules (or any other suitable product formulation) which comprise one or more high-volume swelling hydrogels (these may be the same or different from those in taken in the initial high dose) at time intervals of around at least 12 hours and preferably around at least 24 hours, and highly preferably longer e.g. around 48 hours. Preferably, the high-volume swelling hydrogel-containing product formulation will be retained within the patient's stomach for several days (1-7 days), further preferably for several weeks (1-30 weeks) or even longer. The optional second and subsequent doses may be the same as or different from each other.

Ideally the above method will also include the ingestion by the patient of one or more of: at least 300 Kcal of foodstuffs and at least 100 ml of water, before and/or during and/or after the ingestion of the at least one of the first, second or further subsequent doses by the patient.

In a still further aspect of the present invention, the invention optionally includes use of one or more "stiffeners" embedded in the high-volume swelling hydrogel, especially when it is in the form of a compressed flat sheet, as described above. These one or more "stiffeners" will preferably be made from the same components as the high-volume swelling hydrogel but in a different ratio that ensures that the stiffener swells less than the main body. The purpose of the stiffeners is to reduce the likelihood that the unexpanded material will exit the stomach into the duodenum too early.

The proposed stiffeners will provide particular benefit to compressed flat sheet when it is rolled (for example into a "swirl") prior to inserting into a capsule casing. Preferably the stiffeners are embedded in the flat sheet in one or more orientations relative to the plane of the flat sheet to prevent the flat sheet from bending in at least one direction. The one or more stiffeners will assist in controlling the rolled material to make it easier to insert into a capsule casing and also they will useful to assist in providing rigidity to the rolled material particularly when the SPH is in its unexpended state, i.e. it will be restricted to unroll longitudinally during the swelling process in the stomach and thereby the longitudinal edges will be prevented from before rolling or curling in on themselves in a lateral direction.

In another further aspect, the present invention also includes attaching the endcaps of the capsule casing to the inserted rolled sheet of high-volume swelling hydrogel, the endcaps dissolve very quickly on entering the stomach allowing the rolled hydrogel to unroll. The attachment may be provided using any suitable fixing or gluing means provided it does not interfere with the dissolution of the endcaps and the unrolling of the rolled hydrogel sheet.

In a yet further aspect, the present invention also provides a method to prepare a sheet of high-volume swelling hydrogel embedded with one or more "stiffeners", comprising the steps:

a) providing a first hydrogel (an initial first hydrogel), preferably a first superporous hydrogel, which comprises a plurality of pores which are defined by an interpenetrating network, or a semi-interpenetrating network or a simple cross-linked structure, and which is made from a composition comprising one or more hydrophilic polymers, optionally one or more biocompatible polymers and optionally one or more plasticising agents;

b) providing a second hydrogel (an initial second hydrogel), preferably a second superporous hydrogel, which comprises a plurality of pores which are defined by an interpenetrating network, or a semi-interpenetrating network or a simple cross-linked structure, and which is made from a composition comprising one or more hydrophilic polymers, optionally one or more biocompatible polymers and optionally one or more plasticising agents; wherein the coefficient of stiffness for the second hydrogel is greater than the coefficient of stiffness for the first hydrogel;

c) create strands of the second hydrogel and suspend these across a container or tray; d) fill the container or tray with the first hydrogel until the strands of the second hydrogel are at least partially immersed therein, to yield a composite hydrogel;

e) optionally treating the composite hydrogel provided in step d) under suitable conditions to improve its plasticity, to yield a plasticised composite hydrogel; and f) treating the composite hydrogel or the plasticised composite hydrogel, obtained from either step d) or step e) respectively, with a compressive force suitable to collapse and/or flatten at least some of the pores of the initial or plasticised, first and second hydrogels without substantially breaking the interpenetrating network, or a semi-interpenetrating network or a simple cross-linked structure thereby to yield the sheet of high-volume swelling hydrogel embedded with one or more "stiffeners".

The present invention also provides an alternative method to prepare a sheet of high-volume hydrogel embedded with one or more "stiffeners", comprising the steps:

a) providing container with an open mouth, and suspending one or more removable rods suspended across the open mouth of the container;

b) pouring an amount of a hydrogel (an initial first hydrogel) preferably a first superporous hydrogel, which comprises a plurality of pores which are defined by an interpenetrating network, or a semi-interpenetrating network or a simple cross-linked structure, and which is made from a composition comprising one or more hydrophilic polymers, optionally one or more biocompatible polymers and optionally one or more plasticising agents into a container, until the level of the first hydrogel is sufficient to at least partially immerse the suspended removable rods;

c) allowing the first hydrogel to set;

d) removing the removable rods; and e) filling the spaces in the gelled hydrogel which are formed by the absence of the removable rods with an inert filler material (for example an inert cement material) which is preferably water and/or acid soluble.

DESCRIPTION OF THE DRAWINGS

The invention will now be described with reference to the representations in the following Figures, in which.

DETAILED DESCRIPTION

Figure 1:
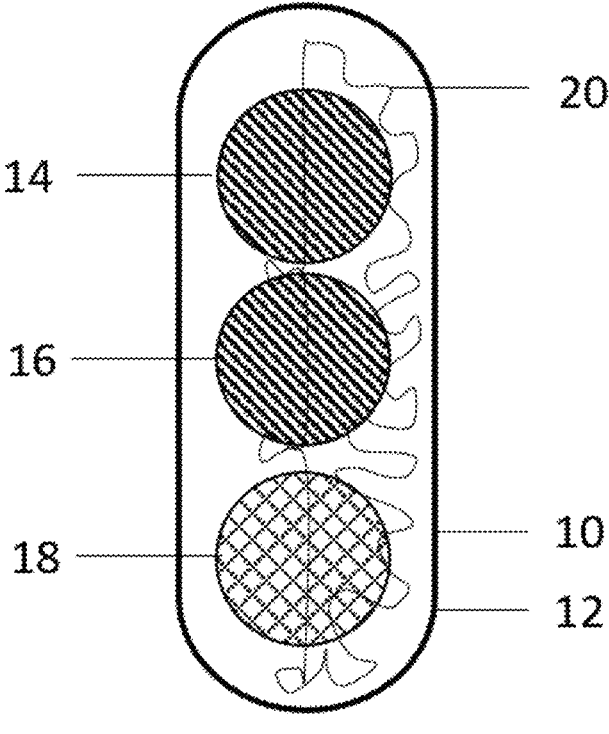
FIG. 1 shows a first example product formulation which includes a string of hydrogel "beads"

Referring to FIG. 1, this depicts an elongate capsule 10 having a capsule casing 12 which surrounds three hydrogel beads 14, 16 and 18 which are linked together using a thread 20. Hydrogel beads 14 and 16 are made from one or more slow swelling non-superporous hydrogel material, whereas hydrogel bead 18 is made from one or more high-volume swelling hydrogel material.

Figure 2:
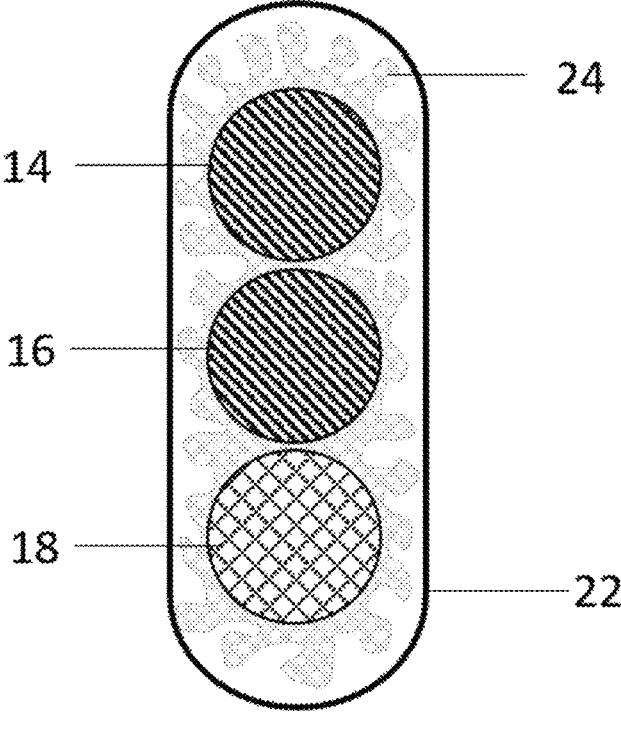
FIG. 2 shows a second example product formulation which includes hydrogel "beads" wrapped in a membrane or mesh.

FIG. 2 shows a similar elongate capsule 22 to that shown in FIG. 1, except that the three hydrogel beads 14, 16 and 18 are wrapped in a stretchable or initially folded membrane or mesh 24, in place of the thread 20.

Figure 3:
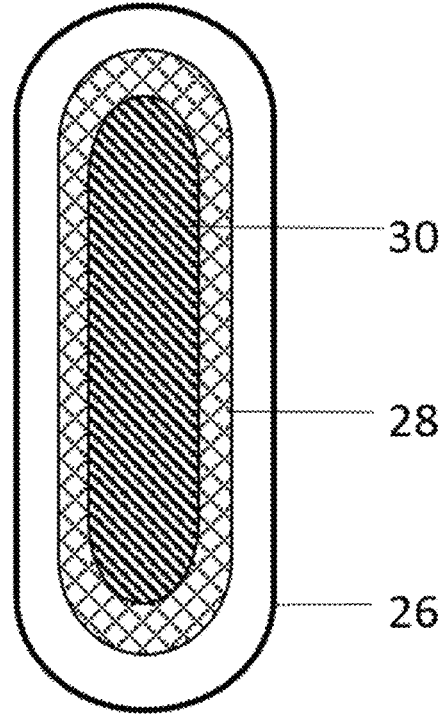
FIG. 3 shows a third example product formulation which includes a "core/shell" arrangement of the hydrogel components.

FIG. 3 shows an elongate capsule 26, which contains a core shell arrangement of hydrogel components, the shell 28 being made from a high-volume swelling hydrogel material, and the core 30 being made from a slow swelling non-superporous hydrogel material.

Figure 5:
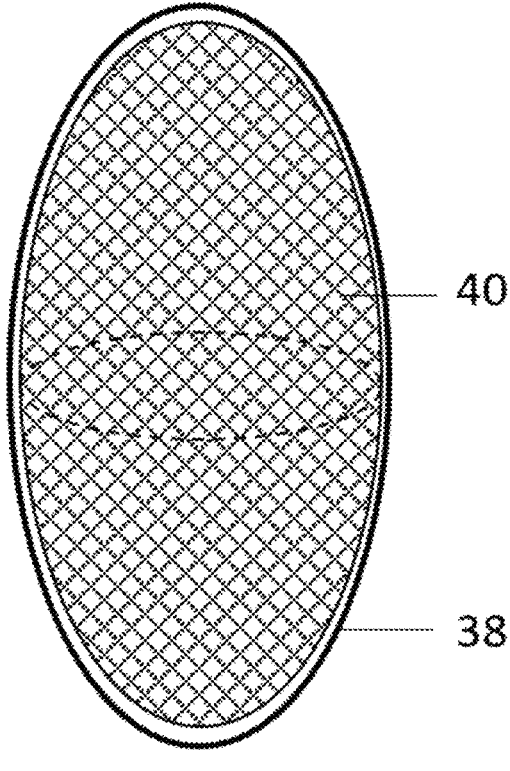
FIG. 5 shows a fourth example product formulation.

FIG. 5 shows an oval shape 'blob' 40 (35 mm-45 mm major axis and 10-15 mm minor axis), which represents a partially hydrogel material which will comprise a swollen flexible high-volume fast swelling superporous hydrogel according to the present invention. The gel is flexible and coated with acid-dissolvable polymers or expandable membrane or mesh 38.

in a conventional freezer or in an ultra-low temperature freezer (−20 C to −86 C). The rapid cooling of ultra-low temperature freezer will result in a sample with a desirably smooth surface. Freeze-dryer can then be used to dry the frozen sample for 24-48 h to thereby create pores.

Depending on composition ratio, freezing process and freeze drying temperature, the pore size ranges from approximately 100 um to 1 mm.

The gelled SPH sample is then plasticised by treating it in a steamed chamber for 0.5 to 2 hours; typically this is a closed containing which contains a small water bath of 40-80 C. The gelled SPH sample is then treated with a compressive force so that its thickness is compressed (dramatically reduced) to $\frac{1}{5}$ to $\frac{1}{10}^{th}$ of its original dimension and it is made into a flat sheet; this dramatic reduction serves to render a much higher volume potential which upon contacting the swelling media, will boost both the swelling rate and the swelling volume ratio. The flat sheet is rolled into a swirl, and the rolled sample state can be fixed by cooling down to room temperature. The rolled sample is then washed in acetone for 10-24 h and left in the vacuum desiccator to dry for 24-48 h.

TABLE 1

| SAMPLE | Volume of 2% w/v CS dissolved in 0.1M acetic acid (ml) | Volume of 4% w/v PVP dissolved in distilled water (ml) | GTA:CS molecular ratio | Concentration and Volume of glutaraldehyde in distilled water | Volume of GTA added (ml) | Compression ratio (initial thickness over final compressed thickness) |
|---|---|---|---|---|---|---|
| 1 | 20 | 10 | 1:10 | 0.4% | 6.25 | 1 |
| 2 | 20 | 10 | 1:10 | 0.4% | 6.25 | 8 |
| 3 | 20 | 10 | 1:10 | 1.2% | 2.08 | 7 |
| 4 | 30 | 10 | 1:10 | 0.4% | 9.38 | 1 |
| 5 | 30 | 10 | 1:10 | 0.4% | 9.38 | 5 |
| 6 | 30 | 10 | 1:10 | 1.2% | 3.126 | 4.5 |

The following process is according to the present invention and is used to prepare the high-volume swelling hydrogels as detailed in Table 1.

Process for the Preparation of High-Volume Swelling Superporous Hydrogels Comprising Chitosan (CS) and Poly (N-Vinyl-2-Pyrrolidone) (PVP)

Ingredients:

Chitosan (CS) dissolved in 0.1M acetic acid (2% w/v).

Poly (N-vinyl-2-pryrolidone) (PVP) dissolved in distilled water (4% w/v).

0.4-2 wt. % glutaraldehyde (GTA) crosslinker in distilled water

Various ratios of the two solutions containing CS and PVP are mixed together (volume ratio of CS solution:PVP solution ranges 5:1 to 1:2), and different amounts of 0.4% GTA (volume ratio of GTA solution:CS solution ranges from 1:0.5 to 1:100) as a cross linking agent of CS is added to the CS/PVP blend as detailed in Table 2 below.

Gelation generally commences upon addition of the crosslinking agent to the mixture of CS and PVP solutions and is left to continue until the mixture in the mould/petri dish/reaction vessel is no longer able to move upon tilting. The higher the concentration, the faster the rate of gelation, typically 0.4% requires up to 12 hours to reach full gelation, whereas 1.2% achieves full gelation in about 10 minutes.

The sample is then covered and left to complete the crosslinking at room temperature over a period of 5-24 h.

Pores of a suitable size may be then created in the gelled sample. This can be achieved by freezing the gelled material Method of Testing The rate of swelling and increase in swelling volume ratio for the gelled samples detailed in Table 1 above were tested as follows:

The swelling media used is simulated gastric fluid (SGF), which per litre contains 2 g sodium chloride, 7 ml hydrochloric acid, various amount of pepsin with an activity of 500 per mg protein from 0 g to 15 g) and the solvent is distilled water. The dimension and the mass of the dry samples will be measured prior to the rolling of the sample. The sample will then be put into SGF media for swelling tests. The measurements of the size and mass of the swollen sample will be made at 30 seconds, 5 min, 30 min and 1 hour and 24 h, 48 h etc. (consecutively once every day to test the its degradation property in SGF). In details, samples will be taken out of the media, and drain until no water dripping down from the sample before the weighing on the scale.

Results

The rate of swelling and the swelling volume ratio ($SR_v = V_s - V_d/V_d$ where $V_s$ represents the volume of SPH sample after immersion in SGF, and $V_d$ is the volume of the SPH sample prior to immersion) for each of the above samples were measured to be as detailed in Table 2 below:

TABLE 2

| SAMPLE | RATE OF SWELLING (VOLUME SWELLING RATIO IN THE FIRST 5 MINUTES) | MAXIMUM SWELLING VOLUME RATIO | SWELLING WEIGHT RATIO |
| --- | --- | --- | --- |
| 1 | 1.4 | 2.5 | 33.4 |
| 2 | 14.0 | 15.3 | 33.6 |
| 3 | 11.6 | 12.6 | 24.9 |
| 4 | 3.15 | 3.21 | 33.2 |
| 5 | 10.5 | 12.7 | 33.8 |
| 6 | 8.0 | 8.4 | 23.4 |

All samples that have been compressed and rolled (2, 3, 5, 6) can open up and flatten into their unmodified state immediately when attaching the swelling media. The samples generated in this method have a superfast swelling rate and can open up automatically in 5-in SGF with a volume swelling ratio of 14-15.

The results demonstrate that a high-volume swelling hydrogel number 2, provides particularly good results.

Discussion of the Results

It is noted that the theoretical extent of improvement of volume swelling ratio will depend on the volume portion of the pores (pore density); the more porous the material the greater the effect will be on increasing swelling volume. The water content in the initial sample has a linear correlation to the maximum swelling volume. This is again because the initial water content determines the volume of pores that can be created within the device system. The water content is controlled by both by the composition of both samples, the concentration of PVP and GTA.

Method of Preparing a High-Volume Swelling Super Porous Hydrogel and a Non-Super Porous Hydrogel from a Basic Hydrogel Composition Comprising Acrylamide and Alginate Starting Materials.

The Acrylamide (0.5-4.0M), Alginate (0.08-1.2M), N,N'-bis(acryloyl)cystamine (0.3-8.0 mM), Ammonium persulfate (1.2-40.0 mM), Tetramethylethylenediamine (1.2-40.0 mM) are dissolved and mixed together in distilled or deionized water. The mixture is then poured into moulds of a desired shape and size and incubated at 50-60° C. for 30 min to 2 hours and then left at room temperature for 24-48 hours to allow for the reaction (formation of the hydrogel) to go to completion. The set samples are then removed from the moulds and soaked in calcium chloride (10%-40% w/v) for 1 minutes to 1 hour with vigorous stirring. The treated samples are then washed intensively to get rid of any unreacted residual starting materials, loosely covered and dried slowly at room temperature.

Completely dried samples of the resulting basic hydrogel are used directly as a mechanically strong slow swelling non-super porous hydrogel.

Partially dried samples of the resulting basic hydrogel are converted into a high-volume swelling hydrogel using the following further treatment steps. Firstly, a sample of the basic hydrogel is treated using a freeze-drying process to obtain a super porous hydrogel, by freezing a sample of the basic hydrogel at –20° C. to –86° C. for 5-24 hours and then transferred to the freeze-drying chamber to complete the lyophilization under vacuum for 24-48 hours. The resulting freeze-dried samples (super porous hydrogel) are then plasticised by treating with steam in the water bath at temperature of 40-70° C. for 20-60 min. Finally, the high volume-swelling hydrogel is compressed at the preferred swelling direction in order to minimise the initial volume of the sample and to maximise its swelling capacity.

Experiment to Determine the Optimum Plasticising Conditions for Making High Volume Swelling Superporous Hydrogels of the Present Invention Five samples of initial hydrogel (Acrylamide (AAm)/Alginate) were prepared using the general composition detailed in Table 3 below.

TABLE 3

| AAm | Alginate | MBA | APS/TEMED | CaSO$_4$ |
| --- | --- | --- | --- | --- |
| 100 mM | AAm:Alginate 6:1 w/w | 0.1 mM | 0.5 mM | 1.8 mM |

An amount of water was then added to each sample before it was freeze dried; the amount of water and freeze drying conditions for each sample is detailed below in Table 4.

TABLE 4

| Sample # | #0-20C | #5-20C | #10-20C | #15-20C | #20-20C | #0-50C | #5-50C | #10-50C | #15-50C | #20-50C | #15 |
| --- | --- | --- | --- | --- | --- | --- | --- | --- | --- | --- | --- |
| H$_2$O content (w/w) | 87.5% | 89.6% | 90.3% | 91.3% | 92.1% | 87.5% | 89.6% | 90.3% | 91.3% | 92.1% | 91.3% |
| Freeze-drying temperature (° C.) | –20 | –20 | –20 | –20 | –20 | –50 | –50 | –50 | –50 | –50 | — |

Figure 4:
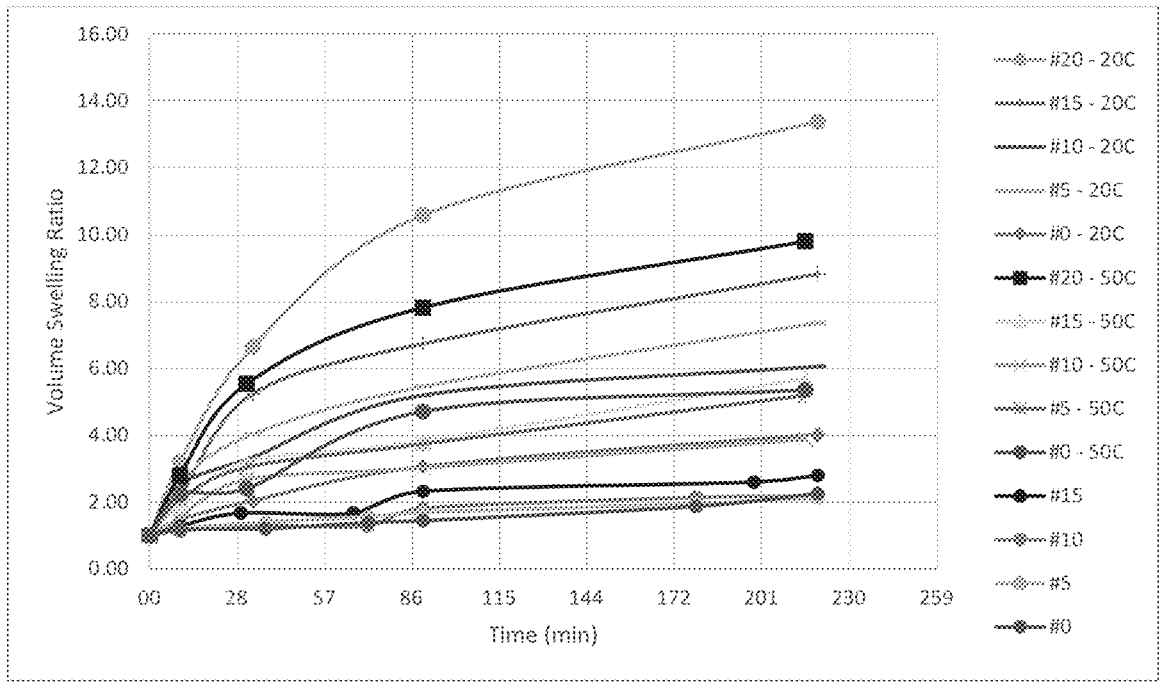
FIG. 4 shows a graph of volume swelling ratio against time for a number of AAm/alginate high-volume swelling hydrogel samples that have been subjected to a range of plasticising conditions.

The resulting plasticised AAm/Alginate samples were then compressed by the ratio 2:16 and as demonstrated in FIG. 4, the plasticising conditions have a profound impact on the volume and rate of swelling with the samples #20-20C (92.1% by wt of water and freeze drying at –20° C.) and #20-50C (92.2%/wt of water and freeze drying at –50° C.) providing the most favourable high-volume swelling superporous hydrogels.

CONCLUSIONS AND ADVANTAGES OF THE PRESENT INVENTION

The fast rate of swelling and excellent high swelling volume achieved by the hydrogel materials of the present invention yield hydrogels and hydrogel-containing compositions which may solve the conventional conflict between volume swelling ratio and swelling rate.

These advantages are particularly seen when hydrogel materials, preferably superporous hydrogel materials, are compressed and rolled after plasticization by water vapour.

Tablets comprising/made using the hydrogel materials of the present invention can be taken without the supervision of a doctor and are therefore truly 'procedureless'.

The polymer formulation can be easily designed to ensure that the resulting high-volume swelling hydrogel stays in the stomach for predetermined and/or a wide range of time.

The formulation of the high-volume swelling hydrogel can be designed to be chemically degradable in the stomach over a predetermine period of time, for example 7 days. Patients can add in more pills or take less pills to customized the strength and duration of the weight control process.

The weight control process can be terminated by FDA-approved chemicals or natural food resources. For example, 10 mg/ml or higher pepsin is found to degrade CS-PVP semi interpenetrating network SPH. For a material which expands 15 folds of its dry volume, the amount of water will be around 93.3% by volume, and such a material will exhibit relatively low mechanical properties which are expected to allow the modified SPH material to be broken down by stomach movement. However, it is likely that the precise termination chemical and mechanism will be different depending on the chemical formulation of the high-volume swelling hydrogel.

The remaining pores that have not been filled up with water of the swollen high-volume swelling hydrogel will enhance the retentive properties of the hydrogel while keeping it floating just below the surface of the gastric fluids. Further, the mechanical properties of the hydrogel are designed to allow it to withstand the gentle movement of the upper stomach without over-pushing the stomach walls thereby avoiding unnecessary discomfort to the patient. A stomach retentive dosage form is a form of design, the aim of which is to make a pill that will stay in the stomach for a desired period without passing out of the duodenum. It is reported that the device that cannot pass into the duodenum should have a size of either 20*50 mm or a diameter of 30 mm. For this to be possible, the stomach retentive dosage form needs to be:

Expandable system (which swells in the stomach fluid immediately to a size that cannot pass out of the stomach or into the duodenum)

Floating system (floating at the top of the stomach to prevent exiting the stomach)

'Open-up' system (opens up to a larger size, usually, from a folded shape, in order to reach the size that is larger than the diameter of duodenum)

The invention in this patent actually meet all these criterions. We aim to make a device that is originally 20*50 mm, with a thickness of 10 mm. Then by compressing to a size around 20*50*1 mm and roll it into a shape that can be put into a capsule. When opening up and expanding, it should have a much larger size (approx. 20*70*12) than the criterion and it will also float.

The invention claimed is:

1. A dosage regimen comprising the step of administering to a patient, suffering from being overweight, having obesity, having diabetes, or a combination thereof, wherein dosage regimen comprises:
   a first dose of a product formulation, which is retained in the stomach of the treated patient for at least one day; wherein the product formulation comprises:
      one or more compressed superporous hydrogels comprising a plurality of pores which are defined by a network structure formed by one or more hydrophilic polymers arranged in the form of one or more selected from an interpenetrating network, a semi-interpenetrating network and a simple cross-linked arrangement,
      wherein at least some of the plurality of pores are collapsed and wherein the network structure which defines the collapsed pores is at least 50% unbroken,
      wherein one or more of the hydrophilic polymers are made by the polymerisation and/or copolymerisation of one or more monomers selected from the group consisting of C1-C6-alkenyl amides and C1-C6-alkenyl acids, and
      wherein the one or more compressed superporous hydrogels will swell to a diameter of $\geq 25$ mm within 10 to 30 minutes of ingestion by the patient;
   wherein the first dose comprises the one or more compressed superporous hydrogels in an amount which will swell to fill up to 80% of the volume of the treated patient's stomach.

2. The dosage regimen according to claim 1 further comprising administering to the patient a second dose of the product formulation, which is retained in the stomach of the treated patient for at least one day, the second dose comprising one or more compressed superporous hydrogels in an amount which will swell to maintain up to 80% of the volume of the treated patient's stomach to be filled.

3. The dosage regimen according to claim 2 further comprising administering one or more further doses of the product formulation, at time intervals of at least 12 hours, which are retained in the stomach of the treated patient for at least one day, the one or more further doses comprising one or more compressed superporous hydrogels.

4. The dosage regimen according to claim 1 further comprising a step of administering the treated patient with at least 100 ml of water during and after ingestion of the first dose.

5. The dosage regimen according to claim 4 further comprising a step of administering the treated patient with at least 300 kcal of foodstuffs during and after ingestion of the first dose.

6. The dosage regimen according to claim 1 wherein the product formulation is retained within the treated patient's stomach for up to 7 days.

7. The dosage regimen according to claim 1 wherein the product formulation is retained within the treated patient's stomach for up to 30 weeks.

8. The dosage regimen according to claim 1 wherein the product formulation further comprises one or more non-superporous hydrogels.

9. The dosage regimen according to claim 1 wherein the product formulation further comprises one or more superporous hydrogels that have not been treated with a compressive force.

10. The dosage regimen according to claim 1 wherein the first dose of the product formulation is administered in an amount which will swell upon ingestion to fill up to 60% of the volume of the treated patient's stomach.

11. The dosage regimen according to claim 1 wherein the first dose of the product formulation is administered in an amount which will swell upon ingestion to fill up to 50% of the volume of the treated patient's stomach.

12. The dosage regimen according to claim 2 wherein the second dose of the product formulation is administered in an amount which will swell upon ingestion to maintain up to 60% of the volume of the treated patient's stomach to be filled.

13. The dosage regimen according to claim 3 wherein the time intervals are at least 24 hours.

14. The dosage regimen according to claim 3 wherein the time intervals are at least 48 hours.

15. The dosage regimen according to claim 1 wherein the one or more compressed superporous hydrogels swell to a diameter >30 mm within 10 minutes of ingestion.

16. The dosage regimen according to claim 1 wherein the one or more hydrophilic polymers further comprise one or more selected from methylcellulose, ethylcellulose, n-propylcellulose, hydroxyethylcellulose, hydroxy-n-propylcellulose, hydroxy-n-butylcellulose, hydroxypropylmethylcellulose, ethylhydroxyethylcellulose, carboxymethylcellulose, carboxymethylstarch, chitosan, alginate, gelatin, cationic dextran, dimethyl aminodextran, diethyl aminodextran, cationic dextrin, polyetherimide, heparin, hyaluronic acid, chondroitin, chondroitin sulfate, heparan sulfate, polygalacturonic acid, polyanuronic acid, polygalacturonic acid polyarabinic acid and polylysine.

17. The dosage regimen according to claim 2 wherein the one or more hydrophilic polymers comprise alginate and the product of the polymerisation and/or copolymerisation of acrylamide.

18. The dosage regimen according to claim 1 wherein the one or more compressed superporous hydrogels are produced by a process comprising a freeze-drying process.

\*    \*    \*    \*    \*